United States Patent [19]
Leason et al.

[11] Patent Number: 5,360,413
[45] Date of Patent: Nov. 1, 1994

[54] NEEDLELESS ACCESS DEVICE

[75] Inventors: Michael H. Leason, Lake Geneva, Wis.; Rick R. Ruschke, McHenry, Ill.; Ralph L. Davis, Genoa City, Wis.

[73] Assignee: Filtertek, Inc., Hebron, Ill.

[21] Appl. No.: 65,234

[22] Filed: May 19, 1993

Related U.S. Application Data

[63] Continuation-in-part of Ser. No. 803,164, Dec. 6, 1991, abandoned.

[51] Int. Cl.$^5$ ................................. A61M 5/00
[52] U.S. Cl. ................................ 604/249; 604/256; 137/843
[58] Field of Search .................... 604/30, 33, 246–247, 604/249, 256; 137/843, 851–852, 854

[56]  References Cited

U.S. PATENT DOCUMENTS

| | | |
|---|---|---|
| 2,999,499 | 9/1961 | Willet . |
| 3,192,949 | 7/1965 | DeSee . |
| 3,385,301 | 5/1968 | Harautuneian . |
| 3,416,567 | 12/1968 | Von Dardel et al. . |
| 3,570,484 | 3/1971 | Steer et al. . |
| 3,726,282 | 4/1973 | Patel . |
| 3,831,629 | 8/1974 | Mackal et al. . |
| 3,994,293 | 11/1976 | Ferro . |
| 4,063,555 | 12/1977 | Ulinder . |
| 4,121,585 | 10/1978 | Becker, Jr. . |
| 4,300,571 | 11/1981 | Waldbillig . |
| 4,324,239 | 4/1982 | Gordon et al. . |
| 4,333,455 | 6/1982 | Bodicky . |
| 4,344,435 | 8/1982 | Aubin . |
| 4,421,296 | 12/1983 | Stephens . |
| 4,496,348 | 1/1985 | Genese et al. . |
| 4,498,658 | 2/1985 | Mikiya . |
| 4,535,820 | 8/1985 | Raines . |
| 4,551,136 | 11/1985 | Mandl . |
| 4,585,435 | 4/1986 | Vaillancourt . |
| 4,596,557 | 6/1986 | Pexa . |
| 4,617,015 | 10/1986 | Foltz . |
| 4,661,110 | 4/1987 | Fortier et al. . |
| 4,675,003 | 6/1987 | Hooven . |
| 4,681,132 | 7/1987 | Lardner . |
| 4,683,905 | 8/1987 | Vigneau et al. . |
| 4,683,916 | 8/1987 | Raines . |
| 4,698,061 | 10/1987 | Makaryk et al. . |
| 4,743,235 | 5/1988 | Waldbillig et al. . |
| 4,749,003 | 6/1988 | Leason . |
| 4,752,287 | 6/1988 | Kurtz et al. . |
| 4,752,292 | 6/1988 | Lopez et al. . |
| 4,776,369 | 10/1988 | Lardner et al. . |
| 4,816,020 | 3/1989 | Brownell . |
| 4,850,978 | 7/1989 | Dudar et al. . |
| 4,874,377 | 10/1989 | Newgard et al. . |
| 4,915,687 | 4/1990 | Sivert . |
| 4,917,668 | 4/1990 | Haindl . |
| 4,935,010 | 6/1990 | Cox et al. . |
| 5,006,114 | 4/1991 | Rogers et al. . |
| 5,048,537 | 9/1991 | Messinger . |
| 5,049,128 | 9/1991 | Duquette . |
| 5,147,333 | 9/1992 | Raines ............................ 604/249 |
| 5,171,230 | 12/1992 | Eland et al. . |
| 5,199,947 | 4/1993 | Lopez et al. . |
| 5,201,715 | 4/1993 | Kling . |

(List continued on next page.)

FOREIGN PATENT DOCUMENTS

WO89/06553 7/1989 WIPO .

OTHER PUBLICATIONS

Cutter OEM Product Catalog, published by Cutter, 20 pages, dated 1990.

(List continued on next page.)

*Primary Examiner*—C. Fred Rosenbaum
*Assistant Examiner*—Corrine Maglione
*Attorney, Agent, or Firm*—Willian Brinks Hofer Gilson & Lione

[57]  ABSTRACT

A needleless access device and method of using the device is disclosed. The needleless access device has a housing having an inlet opening and an outlet opening and a channel formed therethrough. Movably friction fitted in the channel adjacent the inlet opening is a piston. The piston is biased upwardly by a stretchable element. The stretchable element allows the top of the piston to be depressed by a syringe to a level adjacent internal flow channels to permit injection and aspiration of fluids through the device.

39 Claims, 5 Drawing Sheets

U.S. PATENT DOCUMENTS

| | | |
|---|---|---|
| 5,203,775 | 4/1993 | Frank et al. . |
| 5,215,538 | 6/1993 | Larkin . |
| 5,221,271 | 6/1993 | Nicholson et al. . |
| 5,230,706 | 7/1993 | Duquette . |
| 5,242,432 | 9/1993 | DeFrank . |

OTHER PUBLICATIONS

Fluid & Drug Administration Catalog, published by MEDEX Inc., 16 pages, dated 1993.

Advertising entitled "Protect your patients and yourself . . . with SECURE TM," published by MEDEX Inc., 4 pages, dated 1992.

Article entitled, "Caring Alternatives for People With AIDS," 3 pages, undated.

Advertising brochure on Luer Syringe Check Valves, published by Halkey-Roberts, 2 pages, dated 1992.

Advertising for Interlink TM IV, by Baxter, 2 pages, undated.

Advertising for "Quality Check Valves from Burron," 1 page, undated.

Advertising for "Centurion ®–Kleen–Needle/Heplock and All Catheter Connections," published by Tri-State Hospital Supply Corporation, 1 page, undated.

Advertising for BEECH VERSA-LOK TM, 1 page, undated.

Advertising for IMED's Needleless System, 1 page, dated 1993.

Advertising for CLAVE TM –A One Piece Needleless Connector, published by ICU Medical Inc., 1 page, dated 1993. (Three photocopies showing a Clave Needleless Connector are also provided).

Advertising for Click Lock TM Positive Locking IV/-Catheter Connecting Device, and Piggy Lock TM Positive Locking Piggy Back IV Connecting Device, published by ICU Medical, Inc., 1 page, undated.

NEEDLELESS ACCESS DEVICE

CROSS REFERENCE TO RELATED APPLICATION

The present application is a continuation-in-part of application Ser. No. 07/803,164 filed Dec. 6, 1991 now abandoned, which is hereby incorporated by reference.

BACKGROUND OF THE INVENTION

This invention relates to a needleless access device for use with liquid flow and administrative apparatus for medical purposes.

The use of hypodermic needles to inject or withdraw fluids in medical application has been standard practice for a number of years. Even where a patient already has an IV tubing set connected to a vein, hypodermic needles are frequently used to inject fluids into the IV tubing. Often a "Y connector" with a septum is provided in the tubing set for this very purpose. The needle is used to puncture the septum to administer the drug or other fluid, and the septum then sufficiently seals the opening to prevent airborne bacteria from entering the system. Septums are also common on drug vials, where the needle is inserted to withdraw a quantity of the drug.

The widespread use of hypodermic needles leads to numerous needle-stick accidents. These are not only painful, but if the needle is contaminated, could cause serious disease or complications in the needle-stick victim. There is thus a desire for needleless medical systems, where a fluid can be injected or aspirated without the use of a needle, but while maintaining an aseptic system.

U.S. Pat. No. 4,683,916 to Rainer discloses a normally closed reflux valve that allows for the injection and aspiration of fluids when the valve is attached to a syringe. However, the valve has an open inlet area, thus allowing bacterial contamination inside the inlet and on the valve components, which would be swept into the system when a fluid is injected. In addition, this valve is not designed to allow easy aseptic cleaning treatment of the valve's syringe contact surface.

SUMMARY OF THE INVENTION

The present invention includes a needleless access device and a method of using the device.

The needleless access device of the present invention is provided with a piston that, in its normally closed position, seals the inlet opening of the device to prevent bacterial contamination and maintain sterility. The design is conducive to standard septic cleaning of the piston surface which interfaces with the syringe.

Other aspects of the preferred embodiment of the invention include forming the device with a cap having an inlet opening and a body with an outlet opening. A stretchable member provides a biasing force to hold the piston in a closed position. The cap and body are sealed together with a sonic weld with flash traps to prevent particles from contaminating the fluid path. The edge of the stretchable member may be captured between the cap and the body. These and other advantages, and the invention itself, will best be understood in reference to the attached drawings, a brief description of which follows:

DETAILED DESCRIPTION OF THE DRAWINGS AND OF THE PREFERRED EMBODIMENTS OF THE INVENTION

A first preferred embodiment of the needleless access device 10 of the present invention is shown in FIGS. 1–7. The needleless access device 10 comprises a housing 12 made of a cap 14 and a body 16. The housing 12 has an inlet opening 6 and outlet 8. Inside the top portion of cap 14, beginning at inlet opening 6, is a channel 15 forming a fluid passageway through the cap. The channel 15 is tapered so that the channel 15 and inlet 6 form a standard female luer. The outlet 8 is a standard male luer.

Figures 4, 5, 6, 8, 9, 12:
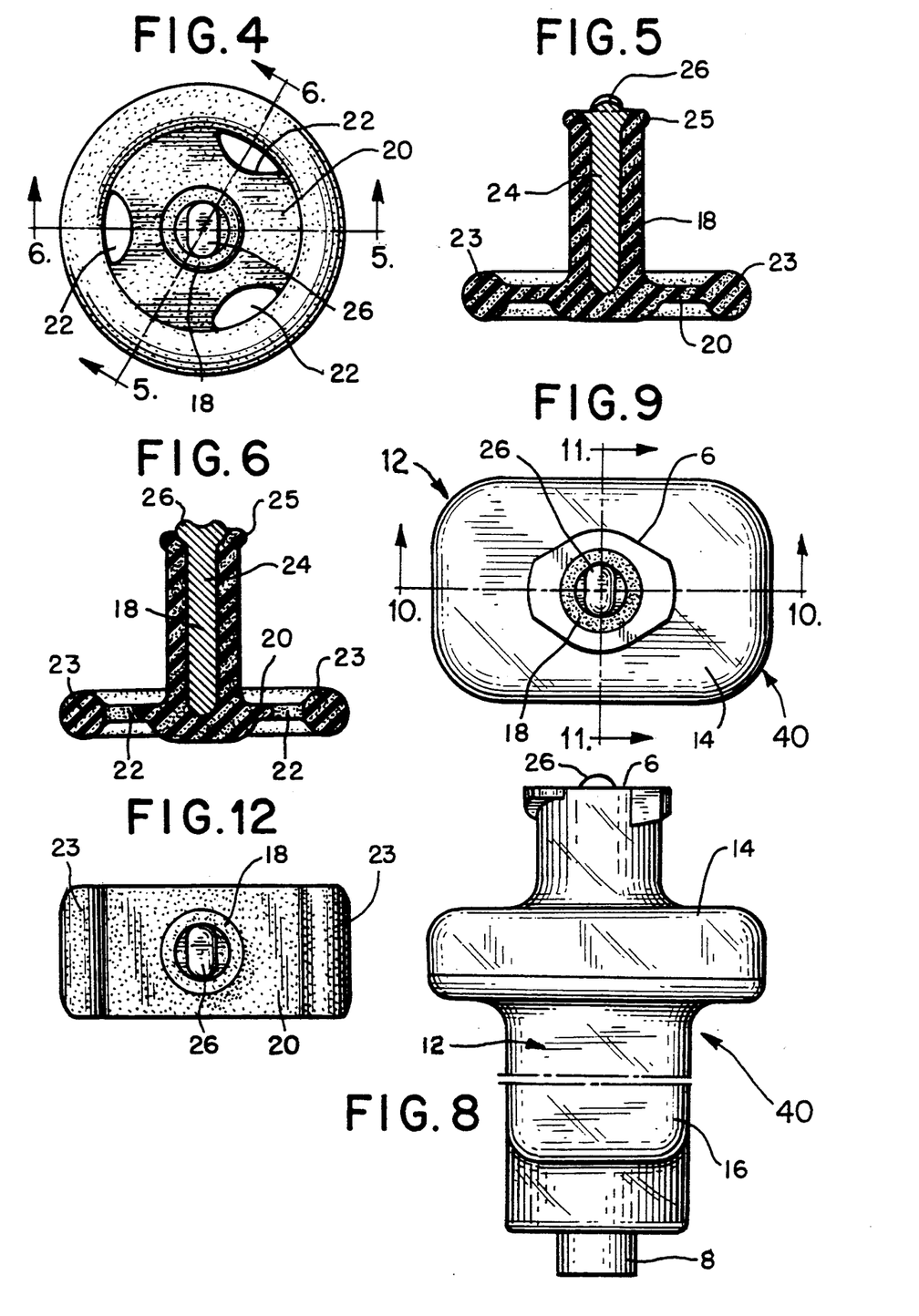
FIG. 4 is a top plan view of the internal piston and stretchable member of the device of FIG. 1.
FIG. 5 is a cross-sectional view taken along line 5—5 of FIG. 4.
FIG. 6 is a cross-sectional view taken along line 6—6 of FIG. 4.
FIG. 8 is a side elevational view of a second embodiment of a needleless access device of the present invention.
FIG. 9 is a top plan view of the device of FIG. 8.
FIG. 12 is a top plan view of the piston and stretchable member of the device of FIG. 8.
Figure 10:
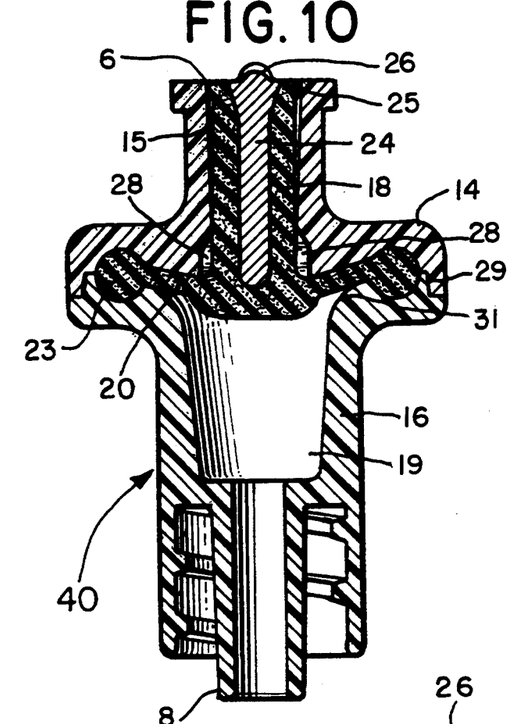
FIG. 10 is a cross-sectional view taken along line 10—10 of FIG. 9.
Figure 11:
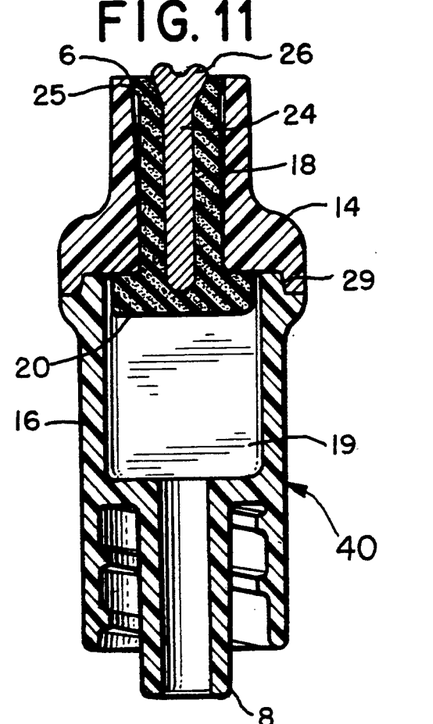
FIG. 11 is a cross-sectional view taken along line 11—11 of FIG. 9.

A piston 18 is biased upwardly by a stretchable element 20 to fill the channel 15. As best seen in FIGS. 4 and 6, the stretchable element 20 is generally round with several holes 22 formed therethrough. In the preferred embodiment, the stretchable element 20 and piston 18 are formed together as a unitary molded item.

Figures 1, 2, 3, 3A, 7:
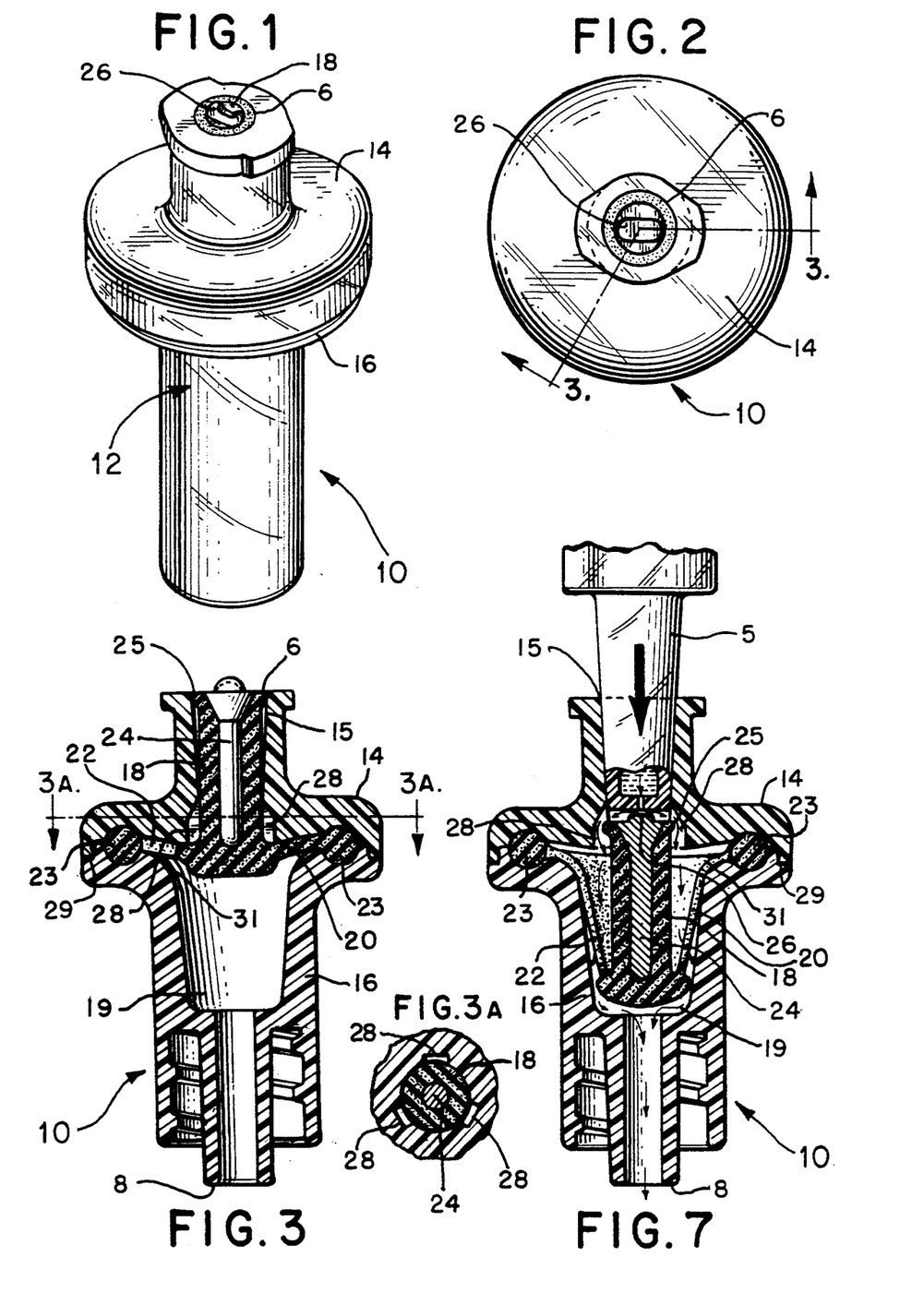
FIG. 1 is a perspective view of a needleless access device of a first embodiment of the present invention.
FIG. 2 is a top plan view of the device of FIG. 1.
FIG. 3 is a cross-sectional view taken along the 3—3 of FIG. 2.
FIG. 3A is a partial cross-sectional view taken along line 3A—3A of FIG. 3.
FIG. 7 is a cross-sectional view like FIG. 3 showing the device of FIG. 1 in its actuated position.

The outside edge of the stretchable element 20 comprises an enlarged area or rib 23 which is used to retain the edge of the stretchable element 20 in the housing 12. As shown in FIGS. 3, 5 and 6, the rib 23 is circular in cross section, and is captured in concave areas formed in the mating surface of the cap 14 and body 16.

The piston 18 of the preferred embodiment has a hole in its central portion which is filled by a pin 24, bonded to adhere the soft piston material to the pin 24. The pin 24 is used to provide rigidity to the piston 18, and transfer forces applied at the top of the pin 24 to the bottom of the piston 18 and the connected stretchable element 20. The top 26 of pin 24 is shaped to prevent occlusion of the end of a syringe or other device used to inject fluid through the housing 12. A wiper seal 25 is provided on the perimeter of piston 18 near its top. The wiper seal 25 acts to seal the top of channel 15 and inlet 6 when the piston 18 is in its normal position. The cap 14 includes three flow channels 28 near the bottom of channel 15, formed longitudinally in the sides of the cap 14 wall forming channel 15.

As best seen in FIG. 7, when a syringe 5 is inserted into inlet opening 6, the tip of the syringe 5 contacts the top 26 of pin 24. As the tip of the syringe 5 is forced into channel 15, the stretchable element 20 thins out as the piston 18 is forced into a cavity 19 formed in body 16. Piston 18 is depressed to a level such that the wiper seal 25 is just below the tops of flow channels 28. Fluid injected by the syringe 5 then flows out the tip, over the top 26 of pin 24, through flow channels 28, through holes 22 in stretchable element 20, into cavity 19 and out through outlet 8. As shown in FIG. 7, the standard male luer tip of the syringe 5 mates with the standard female luer of the inlet 6 and channel 15 to prevent fluid from flowing out of the inlet opening.

Even though not distinctly shown in FIG. 7, since it is a cross sectional view taken through two of the flow channels 28, in the spaces between the three flow channels 28 the wiper seal 25 contacts the side of the cap wall defining channel 15 to keep the piston 18 aligned within the channel 15.

When the syringe 5 is removed, the stretchable element 20 contracts, forcing the piston 18 back upward in channel 15 and seating the openings 22 against the inside of cap 14 to prevent backflow. The inside of cap 14 thus serves as a valve seat and the portion of stretchable element 20 that contacts the cap 14 thus serves as a valve member at the bottom of the piston, producing a valve inside the housing that is normally biased closed by the stretchable element 20. The wiper seal 25 acts to wipe the inside of the channel 15, leaving it in a clean state. The excess fluid left in the flow channels 28 is minimal. The top of piston 18 and top 26 of the center pin 24 can later be aseptically treated before the next injection.

Easy aseptic treatment is facilitated by the placement and configuration of the top surface of piston 18 relative to the inlet opening 6. Preferably the top surface of piston 18 is flush with (as in FIG. 3), or extends outwardly of, the inlet opening 6. In this manner, a cotton ball with disinfectant on it can easily clean the entire surface of the piston over which a medication will pass when injected. It is noted that if the top of piston 18 has other than a flat surface, the equivalent benefit is achieved if the perimeter of the top portion of piston 18 is not inward of the inlet opening 6, meaning that it is either flush with or extends outwardly of the inlet opening 6.

A second embodiment of a needleless access device 40 of the present invention is shown in FIGS. 8-12. The device 40 is generally the same as the device 10 of FIGS. 1-7, and thus similar elements have similar reference numbers. The primary difference is that in device 40, the stretchable element 20 is elongated (FIG. 12) rather than round, and the housing 12 has a generally rectangular cross section (FIG. 9). The edges of stretchable element 20 have a rib 23 (FIG. 10) formed only on the two shorter ends. The cap 14 and body 16 therefore need only have cavities along two sides for capturing the ribs 23.

The stretchable element 20 does not have holes 22 therethrough. Instead, the stretchable element 20 is not quite as wide as the cavity 19 in body 16 (FIG. 11), and fluid injected into the device 40 travels through flow channels 28 and flows around the long sides of stretchable element 20.

Figure 13:
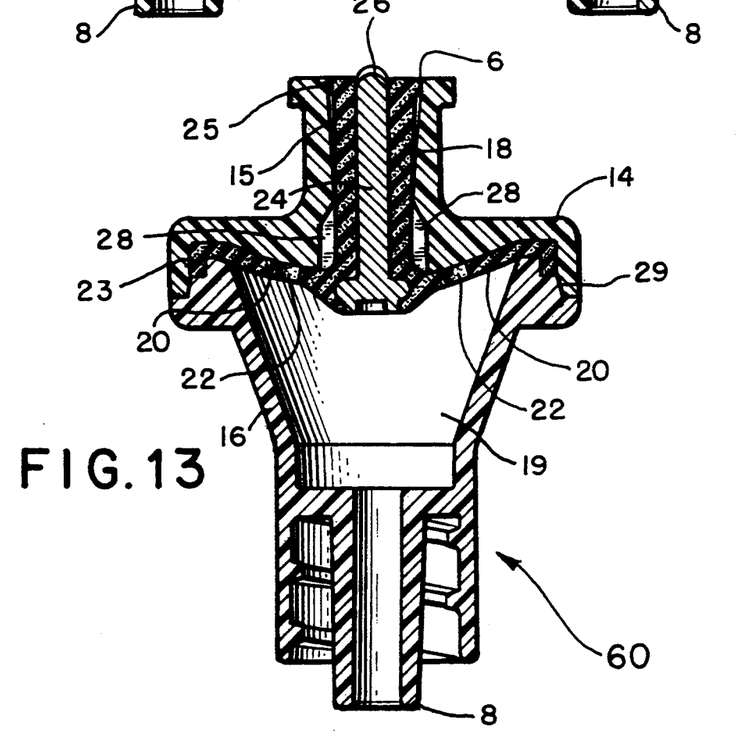
FIG. 13 is a cross-sectional view of a third embodiment of a needleless access device of the present invention.

A third embodiment of the needleless access device 60 of the present invention is shown in FIG. 13. The device 60 is generally the same as device 10 of FIGS. 1-7, and thus similar elements have similar reference numbers. The device 60 uses an insert molded pin 24 in piston 18. The primary other difference is that the rib 23 on the edge of stretchable member 20 has a rectangular cross section, and is thus captured by the cap 14 and body 16 in a slightly different fashion.

Figure 14:
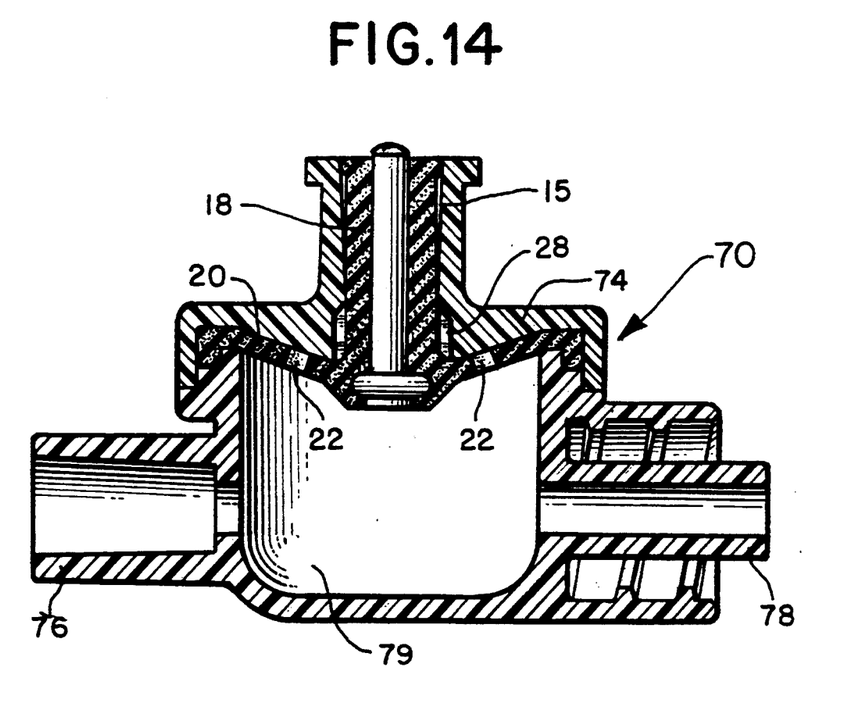
FIG. 14 is a cross-sectional view of a fourth embodiment of a needleless access device of the present invention.
Figure 15:
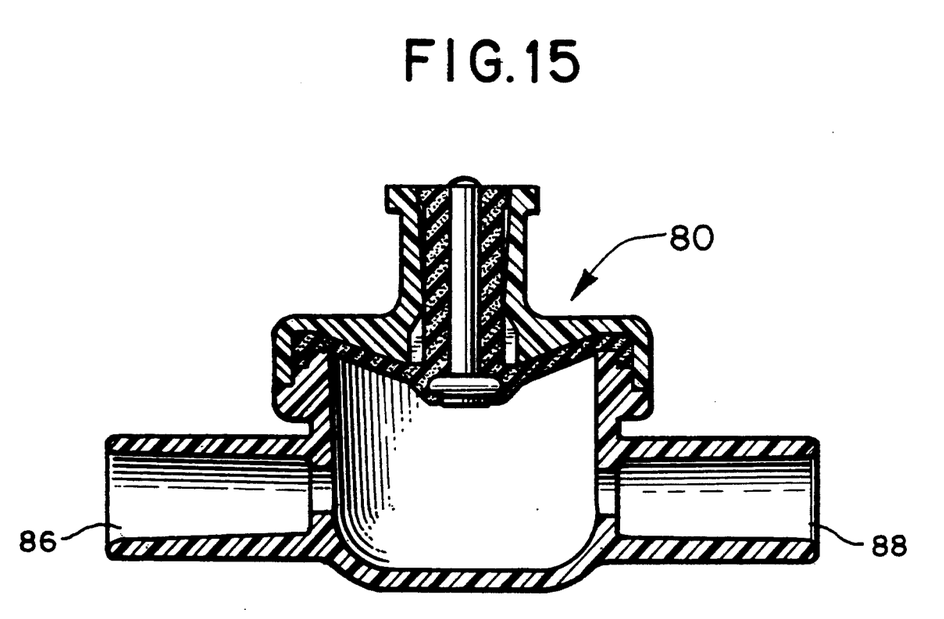
FIG. 15 is a cross-sectional view of a fifth embodiment of a needleless device of the present invention.

While devices 10, 40 and 60 have a single inlet and outlet, the present invention is useable in other configurations. The devices 70 and 80 of FIGS. 14 and 15 respectively may be used in the place of "Y connectors" in IV sets. The device 70 has a standard female luer inlet 76 into chamber 79 and a standard male luer outlet 78. The chamber 79 is fitted with a cap 74 similar to cap 14, that includes a channel 15, flow channels 28, piston 18 and stretchable member 20 with holes 22 therethrough as in device 10. The three port device 70 provides needleless access into an IV tubing set with all the benefits of needleless access provided by device 10. The three port device 70 can also be used as an "add on", connecting directly to the bottom of an IV set.

Figure 16:
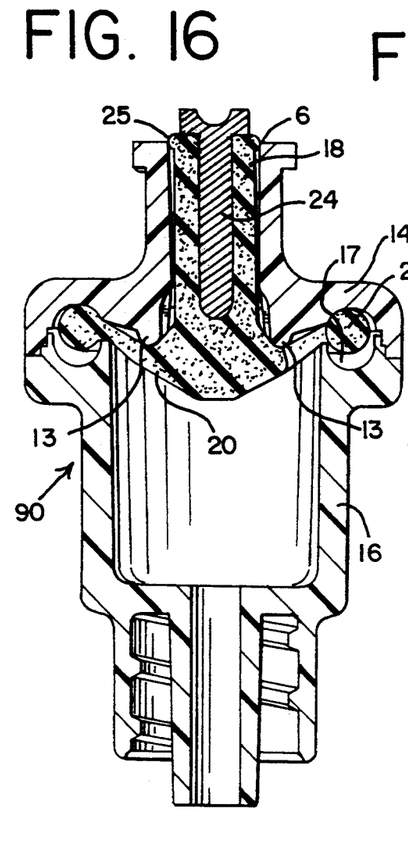
FIG. 16 is a cross-sectional view of a sixth embodiment, which is an improved version of the embodiment of FIGS. 1–7.
Figure 17:
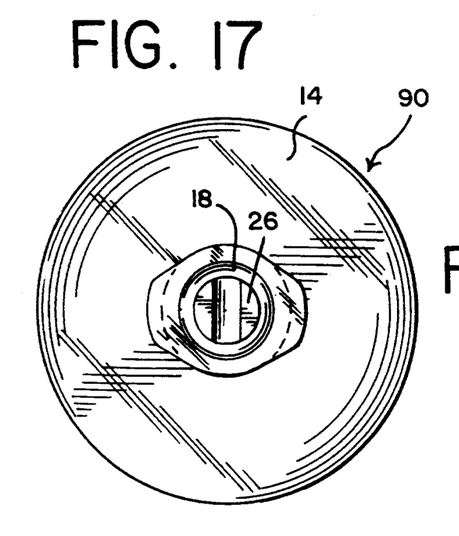
FIG. 17 is a top plan view of the embodiment of FIG. 16.
Figures 18, 19:
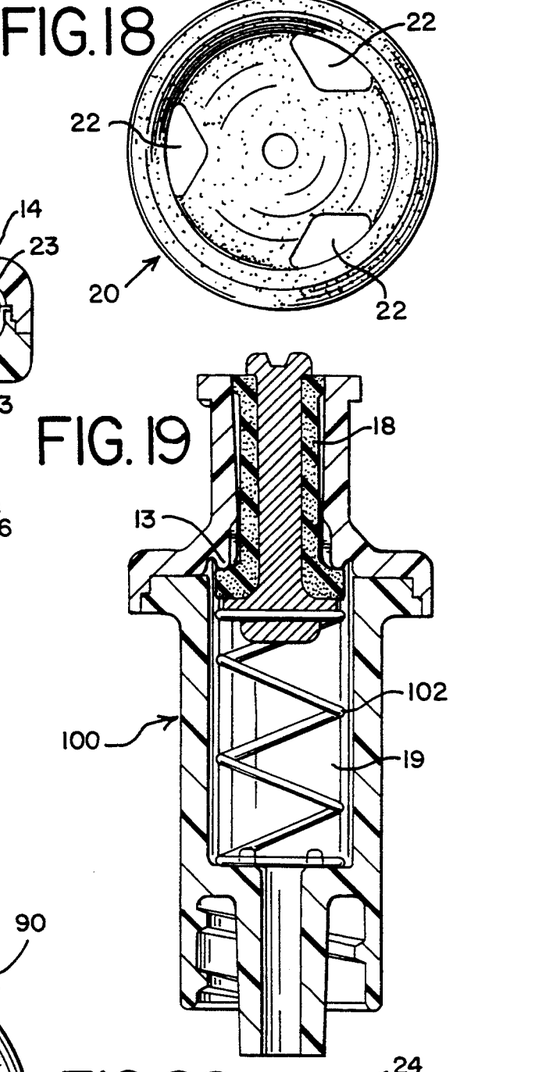
FIG. 18 is a bottom plan view of the stretchable member of the device of FIG. 16.
FIG. 19 is a cross-sectional view of a seventh embodiment of a needleless access device, using a metal spring to provide the biasing force.

Device 80 (FIG. 15) is identical to device 70 except that the inlet 86 and outlet 88 are provided with standard tubing connectors instead of luer connectors so that the device 80 can be used for an IV set in-line connection Device 90 (FIG. 16) is very similar to device 10 of FIGS. 1-7, and thus similar elements have similar reference numbers. There are however, several noticeable improvements. First, pin 24 of device 90 is shaped differently at its top 26 (FIG. 17), though the shape of the top 26 of pin 24 still prevents occlusion of a syringe tip when the device 90 is used. Second, the piston 18 extends outwardly of the inlet 6 when in its biased position. Third, the cap 14 is provided with a sealing ring 13 (which shows up as two downwardly projecting shoulders in cross-section in FIG. 16) at its lower inside diameter to contact with the stretchable element 20 and make a better seal when the piston 18 is in the closed position. Fourth, the concave areas in the cap 14 and body 16 used to capture rib 23 are enlarged to provide a gap 17 around the rib 23, which has been found to allow the stretchable member 20 to contract more easily after use. Fifth, the wiper seal 25 has a more rounded shape, which cooperates with the top of piston 18 extending outwardly of the inlet opening 6. Sixth, as shown in FIG. 18, the holes 22 through the stretchable element 20 of device 90 are shaped slightly different than those shown in FIG. 4 for device 10.

In the preferred embodiments, the cap 14, body 16 and pin 22 are injected molded from a clear, rigid plastic, such as acrylic, polycarbonate or PETG, preferably resistant to solvents such as alcohol. The piston 18 and stretchable member 20 are preferably made of latex rubber or a silicon rubber. These materials have been found to provide a good biasing force with minimal cold flow when the device is used. Other materials that could be used where cold flow is not a concern are Krayton, Sanoprene and Hytrel plastics. Also, the wiper seal 25 preferably provides a good seal without also presenting excess drag when the piston 18 is depressed, or sticking when the piston 18 is released, even though channel 15 is tapered. Harder rubber or plastics are therefore preferred for the wiper seal 25. Thus a two material component may be used, with a soft piston material and harder wiper seal material. The pin 24 is preferably either insert molded into or glued into piston 18.

In the preferred embodiment, the cap 14 and body 16 are sonically welded together, and the joints therebetween are provided with flash traps 29 (FIGS. 3, 7, 10 and 13) to prevent any contaminants from the welding process from entering the fluid contact portions of the device. Also, the inside shoulder 31 of body 16 should be rounded to provide a contoured wall to prevent sharp edges from contacting and cutting or tearing the stretchable material.

The preferred needleless access devices of the present invention have a number of advantages over the prior art, in addition to eliminating the need for needles. First, the inlet is normally sealed, preventing bacterial contamination. Also, the top 26 of pin 24 and the top of piston 18 are generally flush with, and preferably extend outwardly of, the inlet 6 and can easily be aseptically treated before each use. Second, the pin 24 provides rigidity while the rest of the piston 18 and stretchable member 20 is made of a soft material to assure sealing and a good biasing action. Third, the stretchable element 20 is easily positioned and held in place by ribs 23. The cap 14 and body 16 are easily molded with cavities for holding ribs 23 during the assembly process. Fourth, the devices have small hold up volumes, reducing the amount of drug that is wasted. Fifth, the chamber 19 is designed to allow the piston 18 and stretchable member 20 to move up and down without drag or interference.

In addition to the embodiments already depicted, a number of other variations are contemplated. For example, as in FIG. 19 (where again similar elements have like reference numbers), the device 100 has a piston 18 that is biased upwardly by a coil spring 102, preferably in the shape of helical coil, in cavity 19, rather than an elastomeric member with ends captured between top and bottom body housings. In device 100, the valve member comprises a radically extending portion of the bottom of piston 18 which seals against the sealing ring 13.

Figure 20:
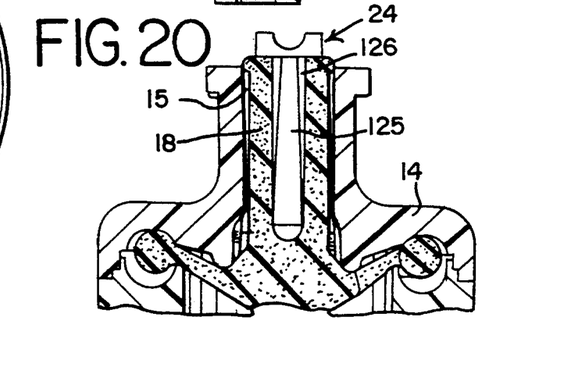
FIG. 20 is a representation of a modified center-core pin useable in the devices of FIGS. 1–7, 8–12, 13, 14, 15, 16–18 and 19.

The support pin 24 of any of devices 10, 40, 60, 70, 80, 90 and 100 could be modified such as shown in FIG. 20 so that the body 125 of the pin 24 tapers as it extends upwardly to provide a gap 126 at the top of the piston 18 between the support pin 24 and the inside of the piston 18. The benefit of this design is that as the piston 18 is forced inwardly, the piston can contract radially into the gap 126 to compensate for the internal luer taper of the channel 15 through cap 14. Of course the same benefit might be achieved by maintaining the shape of support pin 24 and reshaping the piston 18 to provide the gap 126.

Instead of having flow channels 28 in cap 14, the cavity 19 could be sized to allow the top of piston 18 to be depressed below the bottom of channel 15, though in such an embodiment the top 26 of pin 24 or some other member should be designed to maintain the alignment of the piston 18 with the channel 15.

The needleless access could be provided on drug vials and other applications, since aspiration and reverse flow are just as easy as injection through the device.

Of course, other modifications may be made to the preferred embodiments disclosed herein without departing from the scope and spirit of the invention. It is therefore intended that the foregoing detailed description be regarded as illustrative rather than limiting, and that the following claims, including all equivalents, define the scope of the invention.

We claim:

1. A needleless access device comprising:
   a housing having an inlet opening, an outlet opening, and a channel therethrough;
   a moveable piston inside said channel having a top surface and a bottom, the piston being adjacent said inlet opening and biased by a biasing member so that the top surface of the piston is normally generally flush with the inlet opening to facilitate aseptic treatment of the top surface of the piston, the piston comprising a wiper seal formed on a top section of said piston for sealing the inlet opening and wiping the surface of the channel surrounding the piston during actuation and release of the piston; and
   a valve inside said housing comprising a valve member at the bottom of said piston and a valve seat, the valve member normally being biased against said valve seat by said biasing member.

2. The needleless access device of claim 1 wherein the biasing is provided by a stretchable member attached to the piston.

3. The needleless access device of claim 2 wherein said stretchable member has at least one fluid flow opening therethrough.

4. The needleless access device of claim 2 wherein said stretchable member is comprised of rubber.

5. The needleless access device of claim 2 wherein the housing comprises a cap and a body and wherein said stretchable member further comprises one or more ribs captured between said cap and said body to hold said stretchable member in position.

6. The needleless access device of claim 2 wherein the piston and the stretchable member are molded as a unitary member.

7. The needleless access device of claim 2 wherein the biasing is provided by a coil spring.

8. The needleless access device of claim 1 wherein the perimeter of the top surface of the piston is not inward of the inlet opening when the piston is in its biased position.

9. The needleless access device of claim 8 wherein the top surface of the piston extends outwardly of the inlet opening when the piston is in its biased position.

10. The needleless access device of claim 1 wherein said housing comprises a cap and said channel comprises a fluid passageway through said cap defined by a cap wall, the piston being located within said channel, and said cap includes at least one flow channel having an opening into the fluid passageway and formed in the side of the cap wall for allowing fluids injected through said inlet to flow around said piston when the piston is forced to a position just below the opening of said flow channel.

11. The needleless access device of claim 1 wherein said inlet opening and channel form a standard female luer.

12. The needleless access device of claim 1 comprising an additional inlet in fluid communication with said outlet.

13. The needleless access device of claim 1 wherein at least one of said inlet and said outlet comprises a tubing connection.

14. The needleless access device of claim 1 wherein the top surface of the piston is flush with the inlet opening when the piston is in its biased position.

15. The needleless access device of claim 1 wherein the biasing member comprises a stretched elastomeric element and the valve member comprises a portion of the elastomeric element.

16. The needleless access device of claim 1 wherein the biasing member comprises a coil spring and the valve member comprises a radially extending portion of the piston.

17. The needleless access device of claim 1 wherein the valve inside the housing has sufficient sealing force to prevent backflow.

18. A needleless access device comprising:
a) a housing having an inlet opening, an outlet opening and a channel therethrough;
b) a moveable piston having a top surface and a bottom, the piston being adjacent said inlet opening and biased so that the top surface of the piston is normally generally flush with or extends outwardly of the inlet opening; and
c) a center support pin in said piston and protruding out of the top of said piston for transmitting force applied at the top of the pin to the bottom of the piston.

19. The needleless access device of claim 18 wherein said center support pin has a contoured top surface shaped to prevent occlusion of a syringe tip during injection or aspiration of fluid through the device.

20. The needless access device of claim 18 having a gap at the top of the piston between the support pin and the inside of the piston.

21. The needleless access device of claim 18 wherein the center support pin is inserted-molded in said piston.

22. The needleless access device of claim 18 wherein the center support pin is glued into said piston.

23. A needleless access device comprising:
a) a housing having an inlet opening, an outlet opening, and a channel therethrough;
b) a moveable piston inside said channel and having a top surface, the piston being adjacent said inlet opening and biased so that the top surface of the piston is normally generally flush with or extends outwardly of the inlet opening to facilitate aseptic treatment of the top surface of the piston; and
c) a wiper seal formed on a top section of said piston for wiping the surface of the channel surrounding the piston during actuation and release of the piston.

24. The needleless access device of claim 23 wherein the wiper seal contacts the sides of said channel when the piston is fully actuated to keep said piston aligned within said channel.

25. A needleless access device comprising:
a) a housing having an inlet opening, an outlet opening, and a channel therethrough;
b) a moveable piston inside said channel having a top surface, the piston being adjacent said inlet opening and biased so that the top surface of the piston is normally generally flush with or extends outwardly of the inlet opening to facilitate aseptic treatment of the top surface of the piston, the piston comprising a wiper seal formed on a top section of said piston for sealing the inlet opening and wiping the surface of the channel surrounding the piston during actuation and release of the piston; and
c) a stretchable member attached to the piston to provide said biasing, the stretchable member having at least one fluid flow opening therethrough.

26. The needleless access device of claim 25 wherein said inlet opening and channel form a standard female luer.

27. A needleless access device comprising:
a) a housing comprising a cap, the housing having an inlet opening, an outlet opening, and a channel therethrough including a fluid passageway through said cap defined by a cap wall;
b) a moveable piston located within said channel having a top surface and a bottom, the piston being adjacent said inlet opening and biased so that the top surface of the piston is normally generally flush with or extends outwardly of the inlet opening to facilitate aseptic treatment of the top surface of the piston; and
c) the cap including at least one flow channel having an opening into the fluid passageway and formed in the side of the cap wall for allowing fluids injected through said inlet to flow around and past the bottom of said piston when the piston is forced to a position just below the opening of said flow channel.

28. A needleless access device comprising:
a) a housing comprising a cap, the housing having an inlet opening, an outlet opening, and a channel therethrough comprising a fluid passageway through said cap defined by a cap wall;
b) a moveable piston located within said fluid passageway and having a top surface, the piston being adjacent said inlet opening and biased by a biasing member so that the top surface of the piston is normally generally flush with or extends outwardly of the inlet opening to facilitate aseptic treatment of the top surface of the piston;
c) the channel also comprising at least one longitudinal flow channel formed in the side of said cap wall for bypassing said piston; and
d) a valve inside said housing for sealing said longitudinal flow channel to prevent backflow from said outlet to said inlet.

29. A needleless access device comprising:
a housing having an inlet opening, an outlet opening, and a channel therethrough, said housing comprising a cap and a body sealed together by a sonic weld;
a moveable piston having a top surface and a bottom, the piston being adjacent said inlet opening and biased by a biasing member so that the top surface of the piston is normally generally flush with the inlet opening to facilitate aseptic treatment of the top surface of the piston; and
a valve inside said housing comprising a valve member at the bottom of said piston and a valve seat, the valve member normally being biased against said valve seat by said biasing member.

30. A needleless access device comprising:

a housing comprising a cap having an inlet opening therein and a body having an outlet opening therein, the housing having a channel therethrough, the channel comprising a fluid passageway through said body;

a moveable piston having a top surface and a bottom, the piston being adjacent said inlet opening and biased by a stretchable biasing member attached to the piston so that the top surface of the piston is normally generally flush with the inlet opening to facilitate aseptic treatment of the top surface of the piston;

a valve inside said housing comprising a valve at the bottom of said piston and a valve seat, the valve member normally being biased against said valve seat by said biasing member, said body fluid passageway comprising a contoured wall to prevent cutting or tearing the stretchable member during actuation of said piston.

31. A needleless access device comprising;

a cap having an inlet opening and a channel formed therein;

a piston movably friction fitted in said channel and being biased to seal said inlet opening;

a stretchable member connected said piston to provide said biasing; and a body having an outlet opening formed therein, said body attached to said cap, said stretchable member having edges locked between said body and said cap.

32. The needleless access device of claim 31 wherein the cap further comprises one or more flow channels exposed when said piston is forced in said channel in a direction opposite said inlet opening.

33. A needleless access device comprising:

a) a cap having an inlet opening and a channel formed therein;

b) a piston movably friction fitted in said channel and being biased to seal said inlet opening, the piston having a top and bottom, being of a soft material and comprising an insert molded center core pin for providing rigidity to the piston;

c) a stretchable member connected to said piston to provide said biasing; and d) a body having an outlet opening formed therein, said body attached to said cap, said stretchable member having edges locked between said body and said cap.

34. The needleless access device of claim 33 wherein the top surface of the center support pin protrudes out of the top of the piston.

35. A needleless access device comprising:

a) a housing comprising a cap and a body, the housing having an inlet opening, an outlet opening, and a channel therethrough;

b) a moveable piston within said channel and biased toward said inlet opening; and c) a stretchable member attached to the piston to provide said biasing, the stretchable member comprising one or more ribs captured between said cap and said body to hold said stretchable member in a biased position.

36. A method for operating a needleless access device comprising a moveable piston fitted in a cap having an inlet opening and channel formed therein for receiving a syringe, said cap including at least one flow channel having an entrance opening into said channel formed in the side wall of the cap, said piston comprising a wiper seal sealing said channel above the entrance opening to said flow channel and said piston being biased towards the inlet opening by a stretchable member; comprising the step of:

inserting a syringe through said inlet opening and using the syringe to force said piston down said channel to a location where said wiper seal moves past said opening to said at least one flow channel to permit injection and aspiration of fluids through the device.

37. The method of claim 36 further comprising the step of withdrawing the syringe from said inlet opening to allow said stretchable member to contract and seal against said sap to prevent back flow, and to allow said wiper seal to slide along said channel and wipe said channel clean.

38. The method of claim 36 wherein the at least one flow channel is formed longitudinally in the cap wall.

39. The method of claim 36 wherein the inlet opening and channel form a standard female luer and the syringe comprises a standard male luer, and at the location where the wiper seal moves past said opening to at least one flow channel, the female and male luers mate to prevent fluid from flowing out of the inlet opening.

* * * * *

UNITED STATES PATENT AND TRADEMARK OFFICE
CERTIFICATE OF CORRECTION

PATENT NO. : 5,360,413
DATED : November 1, 1994
INVENTOR(S) : Michael H. Leason et al.

It is certified that error appears in the above-indentified patent and that said Letters Patent is hereby corrected as shown below:

In column 1, line 8, delete "1991now" and substitute --1991, now--.

In column 4, line 47, after "connection" insert --.--.

Column 9, line 29, after "connected" insert --to--.

Column 10, line 38, delete "sap" and substitute --cap--.

Signed and Sealed this

Second Day of April, 1996

Attest:

BRUCE LEHMAN

*Attesting Officer*         *Commissioner of Patents and Trademarks*